US006281015B1

(12) United States Patent
Mooney et al.

(10) Patent No.: US 6,281,015 B1
(45) Date of Patent: *Aug. 28, 2001

(54) LOCALIZED DELIVERY OF FACTORS ENHANCING SURVIVAL OF TRANSPLANTED CELLS

(75) Inventors: David J. Mooney, Ann Arbor, MI (US); Robert S. Langer, Newton; Joseph P. Vacanti, Winchester, both of MA (US)

(73) Assignees: Children's Medical Center Corp., Boston; Massachusetts Institute of Technology, Cambridge, both of MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/358,235

(22) Filed: Dec. 16, 1994

(51) Int. Cl.[7] .................................................... C12N 5/00

(52) U.S. Cl. ..................... 435/395; 435/325; 435/405; 424/93.7; 424/457; 424/462; 514/3

(58) Field of Search ................................... 424/93.7, 457, 424/462; 435/325, 395, 405; 514/3

(56) References Cited

U.S. PATENT DOCUMENTS

| | | |
|---|---|---|
| 1,995,970 | 3/1935 | Dorough . |
| 2,609,347 | 9/1952 | Wilson . |
| 2,653,917 | 9/1953 | Hammon . |
| 2,659,935 | 11/1953 | Hammon . |
| 2,664,366 | 12/1953 | Wilson . |
| 2,664,367 | 12/1953 | Wilson . |
| 2,676,945 | 4/1954 | Higgins . |
| 2,683,136 | 7/1954 | Higgins . |
| 2,703,316 | 3/1955 | Schneider . |
| 2,758,987 | 8/1956 | Salzberg . |
| 2,846,407 | 8/1958 | Wilson . |
| 2,951,828 | 9/1960 | Zeile et al. . |
| 3,523,906 | 8/1970 | Vrancken . |
| 3,531,561 | 9/1970 | Trehu . |
| 3,691,090 | 9/1972 | Kitajima et al. . |
| 3,737,337 | 6/1973 | Schnoring et al. . |
| 3,891,570 | 6/1975 | Fukushima et al. . |
| 4,352,883 | 10/1982 | Lim . |
| 4,389,330 | 6/1983 | Tice et al. . |
| 4,440,921 | 4/1984 | Allcock et al. . |
| 4,495,174 | 1/1985 | Allcock et al. . |
| 4,675,800 | 6/1987 | Seki et al. . |
| 4,880,622 | 11/1989 | Allcock et al. . |
| 4,946,938 | 8/1990 | Magill et al. . |
| 5,019,400 | 5/1991 | Gombotz et al. . |
| 5,362,718 | 11/1994 | Kmiecik et al. . |

OTHER PUBLICATIONS

Hansen and Vacanti, "Hepatocyte transplantation using Artificial Biodegradable Polymers", pp. 96–106, Hoffman, M.A., *Current Controversies in Biliary Atresia*, R.G. Landes Company Austin, TX (1993).

Masters, K., *Spray Drying Handbook* (John Wiley & Sons, New York 1984).

Allcock, et al., "Polyphosphazenes with Etheric Side Groups: Prospective Biomedical and Solid Electrolyte Polymers," *Macromolecules* 19:1508–1512 (1986).

Allcock, H.R., et al., Phosphonitrilic Compounds, XV, High Molecular Weight Poly[bis(amino)phosphazenes] and Mixed–Substituent Poly(aminophosphazenes), *Inorg. Chem.* 11:2584–2590 (1972).

Allcock, et al., "Synthesis of Sugar–Subtituted Cyclic and Polymeric Phosphazenes and Their Oxidation, Reduction, and Acetylation Reactions," *Macromolecules* 16:715–719 (1983).

Allcock, et al., "Synthesis of Poly[(amino acid alkyl ester) phosphazenes]$^{1-3}$", *Macromolecules* 10:824–830 (1977).

Allcock, et al., "Glyceryl Polyphosphazenes: Synthesis, Properties, and Hydrolysis," *Macromolecules* 21:1980–1985 (1988).

Allcock, et al., "Amphiphilic polyphosphazenes as membrane materials: influence of side group on radiation cross–linking" *Biomaterials*, 19:500–506 (1988).

Allcock, et al., "Hydrolysis Pathways for Aminophosphazenes," *Inorg. Chem.* 21(2):515–521 (1982).

Allcock, et al., "An Ionically Cross–Linkable Polyphosphazene: Poly[bis(carboxylatophenoxy) phosphazene] an Its Hydrogels and Membranes," *Macromolecules* 22:75–79 (1989).

Asonuma, et al., "Quantitization of Transplanted Hepatic Mass Necessary to Cure the Gunn Rat Model of Hyperbilirubinemia," *J. Ped. Surg.*, 27:298–301 (1992).

(List continued on next page.)

Primary Examiner—Leon B. Lankford, Jr.
(74) Attorney, Agent, or Firm—Clark & Elbing LLP

(57) ABSTRACT

Growth factors and/or angiogenic factors are administered in combination with dissociated cells to be transplanted, preferably in microspheres with the cells on or in a polymeric matrix, to enhance survival and proliferation of the transplanted cells. Examples demonstrate that epidermal growth factor (EGF) was incorporated into microspheres fabricated from a copolymer of lactic and glycolic acid using a double emulsion technique, the incorporated EGF was steadily released over one month in vitro, and it remained biologically active, as determined by its ability to stimulate DNA synthesis, division, and long-term survival of cultured hepatocytes. EGF-containing microspheres were mixed with a suspension of hepatocytes, seeded onto porous sponges, and implanted into the mesentery of two groups of Lewis rats, to demonstrate efficacy in vivo. Two weeks after implantation in PCS animals, devices which included EGF-containing microspheres showed a two-fold increase in the number of engrafted hepatocytes, as compared to implants which received blank microspheres.

9 Claims, 4 Drawing Sheets

OTHER PUBLICATIONS

Barrera, et al., "Synthesis and RGD Peptide Modification of a New Biodegradable Copolymer: Poly(lactic acid–co–lysince,)" *J. Am. Chem. Soc.* 115:11010–11011 (1993).

Benita, et al., "Characterization of Drug Loaded Poly(d, l–lactide) Microspheres," *J. Pharm. Sci.* 73:1721–1724 (1984).

Brown, et al., "Controlled Release of Insulin From Polymer Matrices," *Diabetes* 35:684–691 (1986).

Cohen, et al., "Controlled Delivery Systems for Proteins Based on Poly(Lactic/Glycolic Acid) Microspheres," *Pharm. Res.* 8:713–720 (1991).

Deasy, Patrick, B., *Microencapsulation and Related Drug Processes* (Marcel Dekker, Inc., New York 1984).

Fausto, "Growth Factors in Liver Development, Regeneration and Carcinogenesis," *Prog. Growth Factor Res.* 3:219–234 (1991).

Grolleman, et al., *J. Controlled Release* 3:143 (1986).

Hansen, et al., Hepatocytes transplantation using artificial biodegradable polymers. In: Hoffman, M.A., Ed. Current controversies in biliary atresia. Austin, TX: R.G. Landes, 1993; 96–106.

Higgins and Anderson, "Experimental pathology of the liver." *Arch. Pathol.* 12:186–201 (1931).

Jaffe, et al., "The growth of the liver cells in the pancreas after intra–splenic implantation: the effects of portal perfusion," *Int. J. Exp. Path.* 72:289–299 (1991).

Kaufmann, et al., "Heterotopic hepatocyte transplantation using three dimensional polymers. Evaluation of the stimulatory effects by portacacal shunt or islet cell co–transplantation," *Transplantation Proc.* 26:3343–3345 (1994).

Langer, "New Methods of Drug Delivery," *Science,* 249:1527–1533 (1990).

Mooney, et al., "Transplantation of hepatocytes using porous, biodegradable sponges." *Transplantation Proc.* 26:3425–3426 (1994).

Mooney, et al., "Localized Delivery of Epidermal Growth Factor Improves the Survival of Transplanted Hepatocytes," *Biotech. and Bioeng.* In Press.

Murray, et al., "A Micro Sustained Release System for Epidermal Growth Factor," In Vitro 10:743–748 (1983).

Ricordi, et al., "Trophic factors from pancreatic islets in combined hepatocyte–islet allografts enhance hepatocellular survivial." *Surgery* 105:218–223 (1989).

Sato, et al., "Porous Biodegradable Microspheres for Controlled Drug Delivery. I. Assessment of Processing Conditions and Solvent Removal Techniques," *Pharmaceutical Research* 5:21–30 (1988).

Sluzky, V., et al., "Kinetics of insulin aggregation in aqueous solutions upon agitation in the presence of hydrophobic surfaces" *Proc. Natl. Acad. Sci. USA* 88:9377–9381 (1991).

Starzl, et al., "Medical Progress," *New Eng. J. Med.* 321:1014–1022 (1989).

Uyama, et al., "Delivery of Whole Liver–Equivalent Hepatocyte Mass Using Polymer Devices and Hepatotrophic Stimulation," *Transplantation* 55:932–935 (1993).

Vacanti, et al., "Selective cell transplantation using bioabsorbable artificial polymers as matrices," *J. Ped. Surg.* 23:3–9 (1988).

Wilson, et al., "Ex vivo gene therapy of familial hypercholestremia," *Human Gene Therapy* 3:179–222 (1992).

Vital Statistics of the United States, vol. II(A) (1991).

Annual Report of the Scientific Registry for Organ Transplantation and The Organ Procurement and Transplantation Network, U.S. Department of Health and Human Services, Division of Organ Transplantation (1990).

"Cyanamid Research Develops World's First Synthetic Absorable Suture," *Chemistry and Industry* 95 (1970).

LOCALIZED DELIVERY OF FACTORS ENHANCING SURVIVAL OF TRANSPLANTED CELLS

BACKGROUND OF THE INVENTION

The present invention is generally in the area of cell culture and transplantation and specifically is directed to methods and compositions for enhancing cell survival.

The United States government has rights in this invention by virtue of a grant from the National Science Foundation BCS9202311 to Robert S. Langer.

Liver transplantation is the established therapy for end-stage liver disease, as described by Starzl, et al. *N. Eng. J. Med.* 321:1014–1022 (1989), but this therapy is greatly limited by a scarcity in donor organs. Approximately 30,000 people still die each year in the United States of liver disease (American Liver Foundation, Vital Statistics of the United States, 1988; Vol. 2(A)), and 23% of those listed for transplantation in 1991 died while waiting for an organ (Annual report of the U.S. scientific registry for organ transplantation and the organ procurement and transplant network, 1990. Richmond, Va., UNOS, and Bethesda, Md., the Division of organ transplantation, Health Resources and Services Administration, PE59, 19). Transplantation of parenchymal liver cells, hepatocytes, has been proposed as an alternative to whole organ transplantation for liver disease (Asonuma, et al. *J. Ped. Surg.*, 27:298–301 (1992)). Single metabolic deficiencies may be cured with replacement of 12% of liver mass (Asonuma, et al.), and thus a single liver could be utilized for several patients, or partial resection of a living donor's liver could provide the necessary liver mass to treat another person. Alternatively, a patient's own cells could be harvested, genetically modified, and delivered back to the person to treat single gene defects (Wilson, et al., J. M., Grossman, M., Raper, S. E., Baker, J. R., Newton, R. S., Thoene, J. G. Ex vivo gene therapy of familial hypercholesteremia. *Human Gene Therapy*, 1992; 3:179–222). Hepatocytes have been previously transplanted in suspension, encapsulated, adherent to microspheres, or adherent to degradable or non-biodegradable polymer fibers (Hansen, et al., Hepatocytes transplantation using artificial biodegradable polymers. In: Hoffman, M. A., Ed. Current controversies in biliary atresia. Austin, Tex.: R. G. Landes, 1993; 96–106).

To replace liver function utilizing hepatocyte transplantation, regardless of the means of cell delivery, it will be critical to ensure the survival and growth of the transplanted cells. Previous studies on hepatocyte transplantation have indicated that performing a portal caval shunt (PCS) in conjunction with hepatocyte transplantation improves hepatocyte engraftment (Uyama, et al., *Transplantation* 55:932–935 (1993)). However, patients in liver failure are already in a compromised situation, and the burden of a PCS may not be feasible for this population.

The liver is capable of repeatedly regenerating after partial hepatectomy, and a variety of factors have been identified that induce hepatocyte growth. These include epidermal growth factor (EGF), alpha fibroblastic growth factor, hepatocyte growth factor, and transforming growth factor alpha (Fausto Prog. *Growth Factor Res.*, 3:219–234 (1991)). The effects of these mitogens can be mediated with comitogens such as insulin, glucagon, and estrogen. Many of the factors important in hepatic regeneration appear to be present in the portal circulation (Jaffe, et al., *Int. J. Exp. Path.*, 72:289–299 (1991)), and although the origin of the factors is not clear, trophic factors from islet cells improve the survival of transplanted hepatocytes (Ricordi, et al., *Surgery*, 105:218–223 (1989)). However, it is difficult to attribute these effects to the presence of specific factors, and these approaches are limited by the shortage of available islet tissue. If techniques to reproducibly deliver given amounts of specific factors were developed it would allow one to systematically investigate the effects of various factors, alone and in combination, on hepatocyte survival and growth, and it could potentially move hepatocyte transplantation closer to a clinically relevant therapy.

Systems to deliver macromolecules, such as proteins, over sustained periods have been in active development over the past 20 years, as reviewed by Langer, *Science*, 249:1527–1533 (1990). Delivery vehicles fabricated from biodegradable polymers are especially attractive, as the drug delivery can be controlled by diffusion through the polymer backbone and/or by erosion of the polymer. Systems to deliver factors relevant to hepatocytes, such as insulin (Brown, et al., *Diabetes*, 35:684–691 (1986)) and EGF (Murray, et al., In Vitro, 1983; 10:743–748) have been previously developed. However, small quantities of biologically active factors could be released over extended periods with these systems, but the form of the devices (solid polymer slabs) was not suitable for co-transplantation with cells.

It would therefore be advantageous to have a system for delivery of factors enhancing cell survival, proliferation, and maintaining the cells in a differentiated form which is reproducible, easily manufactured, in a form suitable for implantation with cells, and highly controllable.

SUMMARY OF THE INVENTION

Factors such as EGF are delivered using polymer microspheres to cells such as hepatocytes transplanted into heterotopic sites, to modulate the microenvironment of the transplanted cells to improve engraftment. This approach is useful in studies delineating the role of various factors, both alone and in combination, in hepato-stimulation, as well as treatment of patients in need of cell function replacement or supplementation.

As described in the examples, epidermal growth factor (EGF) was incorporated (0.11%) into microspheres (19±12 $\mu$m) fabricated from a copolymer of lactic and glycolic acid using a double emulsion technique. The incorporated EGF was steadily released over one month in vitro, and it remained biologically active, as determined by its ability to stimulate DNA synthesis, division, and long-term survival of cultured hepatocytes. EGF-containing microspheres were mixed with a suspension of hepatocytes, seeded onto porous sponges, and implanted into the mesentery of two groups of Lewis rats, to demonstrate efficacy in vivo. The first group received a portal-caval shunt (PCS), and the second group did not. Two weeks after implantation in PCS animals, devices which included EGF-containing microspheres showed a two-fold increase in the number of engrafted hepatocytes, as compared to implants which received blank microspheres. Devices implanted into animals without a PCS had fewer engrafted hepatocytes then devices implanted into animals with a PCS. In the non-PCS animals, no difference in the number of engrafted hepatocytes was observed between implants with blank or EGF-containing microspheres. These results demonstrate that it is possible to design systems which can alter the microenvironment of hepatocytes transplanted to heterotopic sites to improve their engraftment. They also indicate that combining EGF with factors from the portal circulation is critical for improving hepatocyte survival.

DETAILED DESCRIPTION OF THE INVENTION

Delivery Systems

Figure 1:
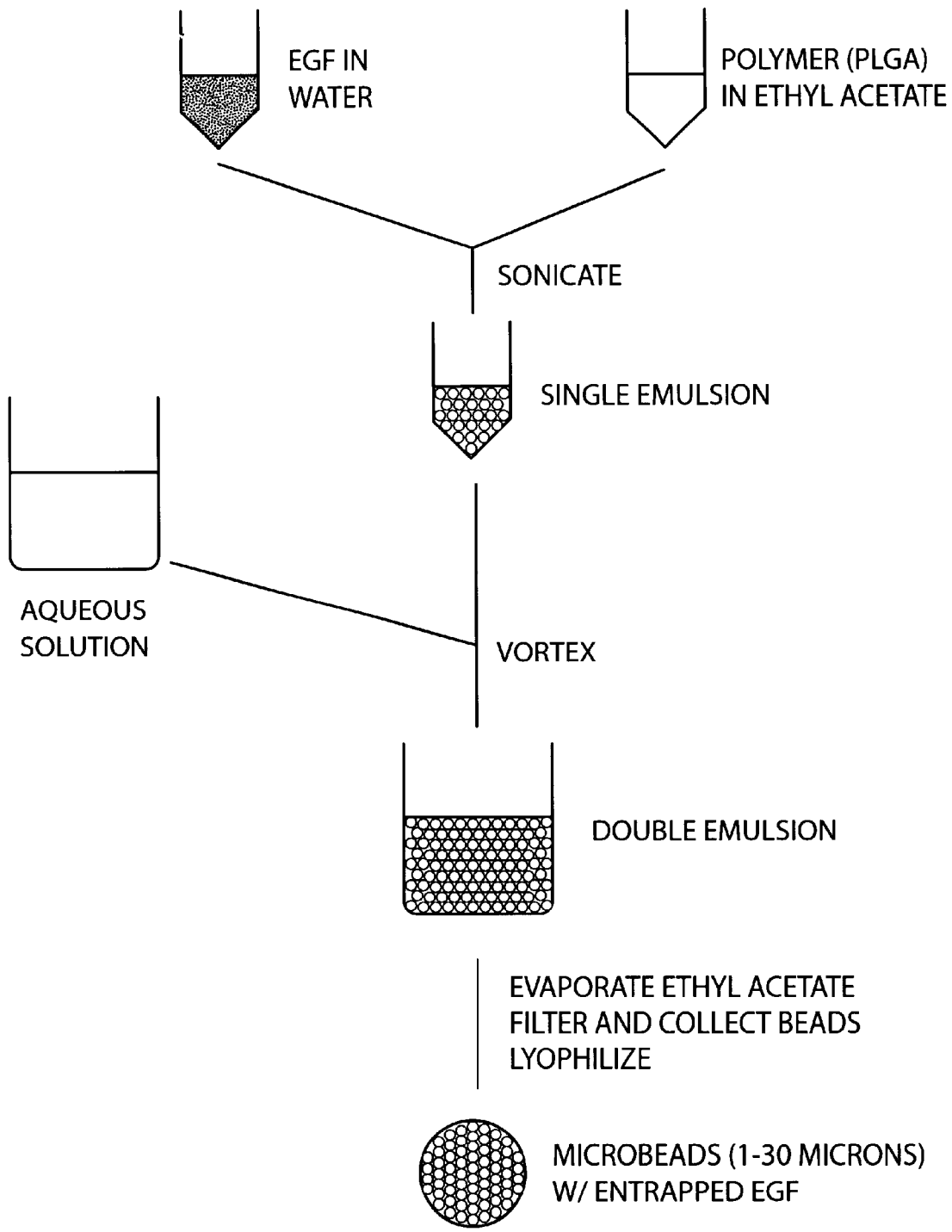
FIG. 1 is a schematic of the process for fabricating microspheres used in Example 1.

Bioactive factors can be provided in a controlled manner using microparticulate delivery systems. In the preferred embodiment, microspheres are utilized to provide controlled release of factors enhancing cell survival, proliferation, or differentiation, to transplanted cells. The polymer microspheres containing the factors are administered to a human or animal, so that the factors are released by diffusion from and/or degradation of, the microspheres. The microspheres are formed of biodegradable polymers, most preferably synthetic polymers or natural polymers such as proteins and polysaccharides. As used herein, polymer refers both to synthetic polymers and proteins. As also used herein, the term "microspheres", indicative of a spherical particle formed of polymer, including a polymer core, includes microcapsules and microparticles, unless otherwise indicated. For use as a delivery system, microcapsules need an outer coating having a selective permeability. Similarly, the bioactive factors must be uniformly dispersed in the microparticles for the microparticles to be used as a delivery system.

Selection of the Synthetic Polymeric Matrix

The term "bioerodible", or "biodegradable", as used herein refers to materials which are enzymatically or chemically degraded in vivo into simpler chemical species.

As noted above, either natural or synthetic polymers can be used as the delivery matrix, although synthetic polymers are preferred for reproducibility and controlled release kinetics. Synthetic polymers that can be used to form the microspheres include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide.

Examples of natural polymers include proteins such as albumin, collagen, synthetic polyamino acids, and prolamines, and polysaccharides such as alginate, heparin, and other naturally occurring biodegradable polymers of sugar units.

PLA, PGA and PLA/PGA copolymers are particularly useful for forming microspheres. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in "Cyanamid Research Develops World's First Synthetic Absorbable Suture", *Chemistry and Industry*, 905 (1970).

Both the release of the incorporated compound and the bioerosion of the matrix are related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both faster release and shorter matrix lives.

The release of the factors from these polymeric systems can occur by two different mechanisms. The drug can be released by diffusion through aqueous filled channels generated in the dosage form by the dissolution of the drug or by voids created by the removal of the polymer solvent during the original microencapsulation. The second mechanism is enhanced release due to the degradation of the polymer. With time the polymer begins to erode and generates increased porosity and microstructure within the device. This creates additional pathways for drug release.

The degradation of the polymers occurs by spontaneous hydrolysis of the ester linkages on the backbone. Thus the rate can be controlled by changing polymer properties influencing water uptake. These include the monomer ratio (lactide to glycolide), the use of L-Lactide as opposed to D/L Lactide, and the polymer molecular weight. These factors determine the hydrophilicity and crystallinity which ultimately govern the rate of water penetration. Hydrophilic excipients such as salts, carbohydrates and surfactants can also be incorporated to increase water penetration into the devices and thus accelerate the erosion of the polymer.

By altering the properties of the polymer and the properties of the dosage form, one can control the contribution of each of these release mechanisms and alter the release rate of Factors. Slowly eroding polymers such as poly L-lactide or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics.

The release rate can also be controlled by varying the loading of factors within the microspheres. Increasing the loading will increase the network of interconnecting channels formed upon the dissolution of the drug and enhance the release of drug from the microspheres.

Additives to Alter Release Rate, Degradation Rate, Stability of Factors

Polymer hydrolysis is accelerated at acidic or basic pHs, so the inclusion of acidic or basic excipients can be used to modulate the polymer erosion rate. The excipients can be added as particulates, can be mixed with the incorporated factors or can be dissolved within the polymer.

Degradation enhancers are based on weight relative to the polymer weight. They can be added to the protein phase, added as a separate phase (i.e., as particulates) or can be codissolved in the polymer phase depending on the compound. In all cases the amount should be between 0.1 and thirty percent (w/w, polymer). Types of degradation enhancers include inorganic acids such as ammonium sulfate and ammonium chloride, organic acids such as citric acid, benzoic acids, heparin, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™.

Pore forming agents to add microstructure to the matrices (i.e., water soluble compounds such as inorganic salts and sugars). They are added as particulates. The range should be between one and thirty percent (w/w, polymer). Excipients can be also added to the factors to maintain its potency depending on the duration of release. Stabilizers include carbohydrates, amino acids, fatty acids, and surfactants and are known to those skilled in the art. In addition, excipients which modify the solubility of Factors such as salts, complexing agents (albumin, protamine) can be used to control the release rate of the protein from the microspheres.

Stabilizers for the factors are based on ratio to the protein on a weight basis. Examples include carbohydrate such as sucrose, lactose, mannitol, dextran, and heparin, proteins such as albumin and protamine, amino acids such as arginine, glycine, and threonine, surfactants such as Tween™ and Pluronic™, salts such as calcium chloride and sodium phosphate, and lipids such as fatty acids, phospholipids, and bile salts.

The ratios are generally 1:10 to 4:1, carbohydrate to protein, amino acids to protein, protein stabilizer to protein, and salts to protein; 1:1000 to 1:20, surfactant to protein; and 1:20 to 4:1, lipids to protein.

Incorporation of Factors into Microspheres.

Microspheres are made by incorporating the factors into a biocompatible polymeric microspheres, wherein the microspheres containing the factors are characterized by sustained controlled release of the factors, preferably over a period of at least 24 hours up to a period of one to two years. In general, the delivery system is designed wherein the bioactive factors are released over a period of between one month and several months. In the preferred embodiment, the polymer is biodegradable, the microspheres have a diameter of less than one hundred eighty microns, most preferably less than seventy microns, and are suitable for administration by injection subcutaneously or intramuscularly (a size suitable for injection through a 23-gauge needle would be less than 180 $\mu$m in diameter), and the microspheres contain from 0.01% by weight up to approximately 30% by weight factors.

As used herein, "micro" refers to a particle having a diameter of from nanometers to micrometers. Microspheres are solid spherical particles; microparticles are particles of irregular or non-spherical shape. A microsphere may have an outer coating of a different composition than the material originally used to form the microsphere. Unless otherwise noted, the term microspheres can be used to encompass microcapsules, and the term microparticles can be used to encompass microparticles, microspheres, and microcapsules. Microparticulates are specifically referred to when describing irregularly shaped polymer or polymer-drug particles. Microcapsules are spherical shaped polymer devices having a non-polymer core or a core of a different polymer than the outer shell. A "composite microsphere" is a microsphere formed of at least two different materials, either a protein and a polymer or two proteins. A "composite" is an aggregation of microspheres made as described herein, bound by materials known to those skilled in the art for this purpose.

As used herein, "sustained" or "extended" release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Factors can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or a combination thereof.

Factors can be incorporated as particulates or by codissolving the factors with the polymer. Stabilizers can be incorporated by addition of the stabilizers to the factor solution prior to formation of the microspheres, Methods for Making Microspheres.

A variety of techniques are known by which active agents can be incorporated into synthetic polymeric microspheres.

Spray Drying

In spray drying, the polymer and factors are mixed together in a solvent for the polymer, then the solvent is evaporated by spraying the solution, leaving polymeric droplets containing the active agent. Spray drying is reviewed in detail by K. Masters in "Spray Drying Handbook" (John Wiley & Sons, New York 1984); and Patrick B. Deasy in "Microencapsulation and Related Drug Processes" (Marcel Dekker, Inc., New York 1984), the teachings of which are incorporated herein. Spray drying may result in some loss of activity due to the heat generated in the process as well as in loss of considerable amounts of the material due to sticking of the polymer to the large surface area on the sides of the chamber, so it is not preferred for labile materials which are available only in small quantities.

Solvent Evaporation

Solvent evaporation techniques can be used to form microspheres. These techniques involve dissolving the polymer in an organic solvent which contains either dissolved or dispersed active agent. The polymer/active agent solution is then added to an agitated continuous phase which is usually aqueous. Emulsifiers are included in the aqueous phase to stabilize the oil-in-water emulsion. The organic solvent is then evaporated over a period of several hours or more, thereby depositing the polymer around the core material. Solvent can be removed from the microspheres in a single step, as described in U.S. Pat. No. 3,737,337 and U.S. Pat. No. 3,523,906, or in U.S. Pat. No. 3,691,090 (under reduced pressure), or by the application of heat, as shown in U.S. Pat. No. 3,891,570. A two-step technique is described in U.S. Pat. No. 4,389,330. Freeze drying has also been used to remove the solvent from microspheres, as reported by Sato, et al, in "Porous Biodegradable Microspheres for Controlled Drug Delivery. I. Assessment of Processing Conditions and Solvent Removal Techniques," *Pharmaceutical Research* 5, 21–30 (1988). The teachings of these methods are incorporated herein.

Solvent evaporation works reasonably well but is not preferred since the amount of incorporated material is usually lower than the theoretical values due to loss of drug to the aqueous phase, as reported by Benita, et al., in "Characterization of Drug Loaded Poly(d,l-lactide) Microspheres," *J. Pharm. Sci.* 73, 1721–1724 (1984).

Phase Separation

Phase separation techniques can also be used to form microspheres. These techniques involve the formation of a water-in-oil emulsion or oil in water emulsion. The polymer is precipitated from the continuous phase onto the active agent by a change in temperature, pH, ionic strength or the addition of precipitants. For example, U.S. Pat. No. 4,675,800, et al., describes the formation of poly(lactic-co-glycolic) acid microspheres containing active proteins. The protein is first dissolved in the aqueous phase of a water-in-oil emulsion or dispersed as a solid in the polymer phase. Polymer is then precipitated around the aqueous droplets or drug particles by addition of a non-solvent for the polymer such as silicone oil. The final product, as with most phase separation techniques, is in the form of a microcapsule. Microcapsules contain a core material surrounded by a polymer membrane capsule. Microcapsules are not the preferred embodiment for delivery of factors, however, since the release kinetics of active agents from these devices can be difficult to control.

Although these phase separation techniques result in the formation of microspheres containing active agents, active agent is often lost during the solvent extraction process. In addition, as with spray drying, biologically active proteins may be denatured during the process.

Rapid Freezing, Solvent Extraction

A method for making microspheres containing factors for delivery and having the desired characteristics is described in U.S. Pat. No. 5,019,400 to Gombotz, et al, the teachings of which are incorporated herein.

There are two principal embodiments of the system for making microspheres: a combination liquified gas—frozen non-solvent system and a frozen non-solvent system.

Polymer and agent to be encapsulated in solution are atomized using an ultrasonic device into a liquified gas. The atomized particles freeze when they contact the liquified gas (liquid nitrogen), forming frozen spheres. These sink to the surface of the frozen non-solvent (ethanol). The liquid gas is evaporated and the spheres begin to sink into the non-solvent as the non-solvent thaws. The solvent in the spheres is extracted into the non-solvent to form microspheres containing the agent to be encapsulated. Other non-solvents such as hexane are added to the non-solvent (ethanol) to increase the rate of solvent extraction from certain polymers, where appropriate, for example, when spheres are formed of polylactide-co-glycolide polymers.

Alternatively, a cold non-solvent for the polymer can be substituted for the combination of liquified gas-frozen no-solvent, provided the temperature of the non-solvent is below the freezing temperature of the polymer/active agent solution. It is important to select a solvent for the polymer having a higher melting point than the non-solvent for the polymer so that the non-solvent melts first, allowing the frozen microspheres to sink into the liquid where they later thaw. If a cold liquid non-solvent system for making the polymeric microspheres is used, the microspheres will sink immediately into the non-solvent. As the solvent in the microsphere thaws, it is extracted into the non-solvent. The solvent for the polymer and the non-solvent for the polymer must be miscible to allow extraction of the solvent from the microspheres.

Bioactive Factors to be Delivered

A variety of bioactive molecules can be delivered using the microspheres described herein. These are referred to generically herein as "factors" or "bioactive factors".

In the preferred embodiment, the bioactive factors are growth factors, angiogenic factors, compounds selectively inhibiting ingrowth of fibroblast tissue such as antiinflammatories, and compounds selectively inhibiting growth and proliferation of transformed (cancerous) cells.

Examples of growth factors include heparin binding growth factor (hbgf), transforming growth factor alpha or beta (TGFβ), alpha fibroblastic growth factor (FGF), epidermal growth factor (EGF), vascular endothelium growth factor (VEGF), some of which are also angiogenic factors. Other factors include hormones such as insulin, glucagon, and estrogen.

Steroidal antiinflammatories can be used to decrease inflammation to the implanted matrix, thereby decreasing the amount of fibroblast tissue growing into the matrix.

Where selective chemotherapeutic agents are available which do not inhibit growth of normal cells, such as antibody targeted chemotherapeutic agents, these can be incorporated into the microspheres and used to inhibit any residual cancer cells remaining following a masectomy or other surgical removal of cancerous tissue before cell transplantation.

These factors are known to those skilled in the art and are available commercially or described in the literature. In vivo dosages are calculated based on in vitro release studies in cell culture; an effective dosage is that dosage which increases cell proliferation or survival as compared with controls, as described in more detail in the following examples. Preferably, the bioactive factors are incorporated to between one and 30% by weight, although the factors can be incorporated to a weight percentage between 0.01 and 95 weight percentage.

Cell-Matrices

The delivery system can be administered with a cell matrix for implantation of dissociated cells or dispersed within a cell suspension which is implanted for cell replacement. In the preferred system, the cells are suspended in, or attached to, a matrix, and then implanted. The microspheres are implanted attached to, or within, the matrix.

Cells

A variety of dissociated cells can be implanted, using standard techniques for isolation and transplantation of tissue or organs, such as livers, with the difference that cells are first dissociated, generally by treatment with a collagenase solution as described below. Autologous cells are preferred, although non-autologous cells can be used with appropriate matching of cell type and use of immunosuppressants such as cyclosporin. In the typical embodiment, the cells are human cells which are implanted into a human. Cells are typically parenchymal cells, i.e., organ cells serving a functional rather than primarily structural function. Examples of organs include liver, pancreas, intestine, uroendothelial cells, including reproductive and urothelial structures, cells forming breast tissue and other soft tissues and endocrine tissues. Cells can also be derived from, or forming, tissues having primarily structural function, such as cartilage (chondrocytes, fibroblasts), tendons (tenocytes), and bone (osteocytes). Cells can be normal or genetically engineered to provide additional or normal function.

Matrices

Two principle types of matrices are described in the literature for creating new tissues or augmenting tissues.

Hydrogel Polymer Solutions

In one embodiment described herein, calcium alginate and certain other polymers that can form ionic hydrogels which are malleable are used to encapsulate cells. The hydrogel is produced by cross-linking the anionic salt of alginic acid, a carbohydrate polymer isolated from seaweed, with calcium cations, whose strength increases with either increasing concentrations of calcium ions or alginate. The alginate solution is mixed with the cells to be implanted to form an alginate suspension. Then the suspension is injected directly into a patient prior to hardening of the suspension. The suspension then hardens over a short period of time due to the presence in vivo of physiological concentrations of calcium ions.

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure:

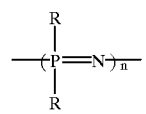

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is crosslinked with dissolved multivalent cations in aqueous media at room temperature or below to form hydrogel matrices.

Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegrable, as used herein, means a polymer that dissolves or degrades within a period that is acceptable in the desired application (usually in vivo therapy), less than about five years and most preferably less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824–830 (1977).

Methods for synthesis and the analysis of various types of polyphosphazenes are described by Allcock, H. R.; et al., *Inorg. Chem.* 11, 2584 (1972);

Allcock, et al., *Macromolecules* 16, 715 (1983);

Allcock, et al., *Macromolecules* 19, 1508 (1986);

Allcock, et al., *Biomaterials*, 19, 500 (1988);

Allcock, et al., *Macromolecules* 21, 1980 (1988);

Allcock, et al., *Inorg. Chem.* 21(2), 515–521 (1982);

Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al.; and Grolleman, et al., *J. Controlled Release* 3, 143 (1986), the teachings of which are specifically incorporated herein by reference.

Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly(acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$-\/\/\/-$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semipermeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Cell Suspensions

Preferably the polymer is dissolved in an aqueous solution, preferably a 0.1 M potassium phosphate solution, at physiological pH, to a concentration forming a polymeric hydrogel, for example, for alginate, of between 0.5 to 2% by weight, preferably 1%, alginate. The isolated cells are suspended in the polymer solution to a concentration of between 1 and 50 million cells/ml, most preferably between 10 and 20 million cells/ml.

Polymeric Matrix

Matrices for implantation can also be formed from the same polymers as used for formation of the microspheres used for delivery of bioactive factors. The polymers are preferably provided as a fibrous structure which had sufficiently interstitial spacing to allow for free diffusion of nutrients and gases to cells attached to the matrix surface. This spacing is typically in the range of 100 to 300 microns, although closer spacings can be used if the matrix is implanted, blood vessels allowed to infiltrate the matrix, then the cells are seeded into the matrix.

For an organ to be constructed, successfully implanted, and function, the matrices must have sufficient surface area and exposure to nutrients such that cellular growth and differentiation can occur prior to the ingrowth of blood vessels following implantation. The time required for successful implantation and growth of the cells within the matrix is greatly reduced if the area into which the matrix is implanted is prevascularized. After implantation, the configuration must allow for diffusion of nutrients and waste products and for continued blood vessel ingrowth as cell proliferation occurs.

Cells can either be implanted after seeding onto a matrix or injected into a matrix already implanted at the desired site. The latter has the advantage that the matrix can be used to prevascularize the site. In this case, the design and construction of the scaffolding is of primary importance. The matrix should be a pliable, non-toxic, injectable porous template for vascular ingrowth. The pores should allow vascular ingrowth and the injection of cells such as hepatocytes without damage to the cells or patient. These are generally interconnected pores in the range of between approximately 100 and 300 microns. The matrix should be shaped to maximize surface area, to allow adequate diffusion of nutrients and growth factors to the cells and to allow the ingrowth of new blood vessels and connective tissue. At the present time, a porous structure that is resistant to compression is preferred for implantation, prevascularization, followed by seeding.

In the preferred embodiment, the matrix is formed of a bioabsorbable, or biodegradable, synthetic polymer such as a polyanhydride, polyorthoester, polylactic acid, polyglycolic acid, and copolymers or blends thereof. Non-degradable materials can also be used to form the matrix. Examples of suitable materials include ethylene vinyl acetate, derivatives of polyvinyl alcohol, teflon, and nylon. The preferred non-degradable materials are a polyvinyl alcohol sponge, or alkylation, and acylation derivatives thereof, including esters. A non-absorbable polyvinyl alcohol sponge is available commercially as Ivalon™, from Unipoint Industries. Methods for making this material are described in U.S. Pat. No. 2,609,347 to Wilson; U.S. Pat. No. 2,653,917 to Hammon, U.S. Pat. No. 2,659,935 to Hammon, U.S. Pat. No. 2,664,366 to Wilson, U.S. Pat. No. 2,664,367 to Wilson, and U.S. Pat. No. 2,846,407 to Wilson, the teachings of which are incorporated by reference herein. Collagen can be used, but is not as controllable and is not preferred. These materials are all commercially available.

Non-biodegradable polymer materials can be used, depending on the ultimate disposition of the growing cells, including polymethacrylate and silicon polymers.

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, mixtures thereof, and other materials known to those skilled in the art of cell culture.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

The present invention will be further understood by reference to the following non-limiting examples. Although described with reference to stimulation of hepatocytes in vitro or implanted in vivo, the methodology and compositions are applicable to transplantation of other cell types.

A system has been developed to release hepatotrophic factors at the site of hepatocyte transplantation. EGF incorporated and released from polymeric microspheres retained its biological activity in vitro, and was able to positively effect the engraftment of hepatocytes transplanted to heterotopic sites. Strikingly, the engraftment of these cells transplanted on biodegradable polymer scaffolds was dependent on the presence of both EGF and factors from the portal circulation, and the delivery of only EGF had little or no effect. These results indicate that the survival of cells transplanted on synthetic scaffolds can be controlled by modulating the local environment, and that this system may also be a useful tool to study liver cell biology in vivo.

Delivery of hepatotrophic factors via sustained release from microspheres is a flexible technique to control the local environment of transplanted cells. A known dose of a factor can be delivered with this approach, and the dose required for a biological effect can be quite small (approximately 10 $\mu$g/animal in this study) because of the localized delivery at the desired site of action. The time over which a drug is released from a polymer matrix, can typically be regulated by the drug loading, the type of polymer utilized, and the exact processing conditions, as discussed above. The release of protein from copolymers of lactic and glycolic acid, such as utilized in this study, is generally controlled by the erosion of the polymer when the protein/polymer ratio is low (Cohen, et al., *Pharm. Res.*, 8:713–720 (1991)). The released protein must also, however, retain its biological activity for this approach to be useful. The biological activity of the EGF incorporated into and released from microspheres in this study did not appear to be adversely effected.

In summary, a system to study the role of specific factors in regulation of cell survival and growth has been developed, which can greatly impact the ability to promote the engraftment of transplanted cells. Furthermore, combining this approach with the design of synthetic extracellular matrices (Barrera, et al., *J. Am. Chem. Soc.*, 115:11010–11011 (1993)) for cell transplantation may allow one to modulate the gene expression of transplanted cells on several levels as they respond to the soluble growth factors (Mooney, et al., (1992)).

EXAMPLE 1

Preparation of Microspheres

MATERIALS AND METHODS

Microsphere Preparation and Characterization.

Microspheres containing EGF were prepared by a modification of a previously described double-emulsion technique (Cohen, et al., (1991)). In brief, a 75:25 copolymer of poly-(D,L-lactic-co-glycolic) acid (Resomer RG 75R, intrinsic viscosity 0.2; Henley Chem. Inc., Montvale, N.J.) was dissolved in ethyl acetate (Fisher Scientific) to yield a 5% solution (w:v). Mouse EGF (Collaborative Research; Bedford, Mass.) was dissolved in water to yield a solution of 2 mg/ml, and 50 $\mu$l of the EGF solution was added to 1 ml of the polymer solution. The polymer/EGF solution was sonicated continuously at 10 watts (Vibracell; Sonics and Materials, Danbury, Conn.) for 15 sec to yield a single emulsion. An equal volume of an aqueous solution containing 1% polyvinyl alcohol (MW 25,000, 88% hydrolyzed; Polysciences Inc., Warrington, Pa.) and 7% ethyl acetate was added to the single emulsion, and the resulting solution was vortexed (Vortex Mixer; VWR) for 15 sec at the high setting to yield the double emulsion. This double emulsion was transferred to a rapidly stirring 250 ml beaker containing 150 ml of an aqueous solution of 0.3% polyvinyl alcohol/7% ethyl acetate. The ethyl acetate was allowed to evaporate over the ensuing 3 hr to yield polymer microspheres with entrapped EGF. The microspheres were then filtered, washed with water, and beads with a size between 32 and 0.4 $\mu$m were collected. The microspheres were lyophilized (Labconco Freeze Dryer, Kansas City, Mo.), and stored at $-20°$ C. until use. Control beads were prepared with the same procedure, but the aqueous solution used to form the first, single emulsion (water in organic) contained no EGF.

To determine the efficiency of EGF incorporation, and the kinetics of EGF release from the microspheres, $^{125}$I-labeled mouse EGF (260 mCi/mg; Biomedical Tech. Inc., Stoughton, Mass.) was utilized as a tracer. Approximately 1 $\mu$Ci of labeled EGF was added to the aqueous EGF solution before formation of the single emulsion, and the beads were prepared as described above. After bead fabrication, a known mass of beads was counted in a LKB CliniGamma 1272 (Wallac, Gaithesburg, Md.), and the incorporated cpm was compared to that of the initial aqueous EGF solution to calculate the percentage of the total EGF that was incorporated into the beads. To determine the release of EGF from microspheres, a known mass of beads (approximately 10 mg) prepared with the labeled EGF were placed in a known volume (2 ml) of phosphate buffered saline (PBS) solution containing 0.1% Tween 20 (Sigma Chem. Co.) and placed in an incubator maintained at 37° C. At set times, the solution was centrifuged to concentrate the beads at the bottom of the vial, and samples (0.1 ml) of the PBS/Tween 20 solution were removed. The sample volume was replaced with fresh PBS/Tween 20 solution. The amount of $^{125}$I-EGF released from the microspheres was determined at each time point by counting the removed sample in a gamma counter, and compared to the $^{125}$I-EGF loaded into the microspheres. The maximum EGF concentration in the release medium (approximately 5 $\mu$g/ml) was well below the maximum solubility of EGF, thus establishing sink conditions for the release study.

Photomicrographs were taken with Polaroid 55 film. The particle size distribution of microspheres was determined using a Coulter Multisizer II (Coulter Electronics, Luton, UK). The process used to make the microspheres is shown diagrammatically in FIG. 1.

RESULTS

A solution of EGF in water was added to a solution containing 5% polymer in ethyl acetate and sonicated to produce the single emulsion of the aqueous EGF solution in the organic phase. This emulsion was added to a larger volume of an aqueous solution containing surfactant and vortexed to form the double emulsion. The beads were mixed rapidly while the ethyl acetate evaporated to prevent microsphere coalescence. The microspheres were subsequently sieved to collect those with a size between 0.4 and 30 µm, lyophilized, and stored before use.

The size of the microspheres was controlled to approximately 20 µm, which is the approximate size of suspended hepatocytes, by varying the concentration of the initial polymer solution. The higher the polymer concentration, the larger the microspheres. A polymer solution of 5% (w:v) yielded an assortment of beads in which the majority were in the desired size range of 10 to 30 µm. Quantitation of microsphere size revealed that the average microsphere size was 19±12 µm. The yield of microspheres with this process was 92±5%.

Figure 2:
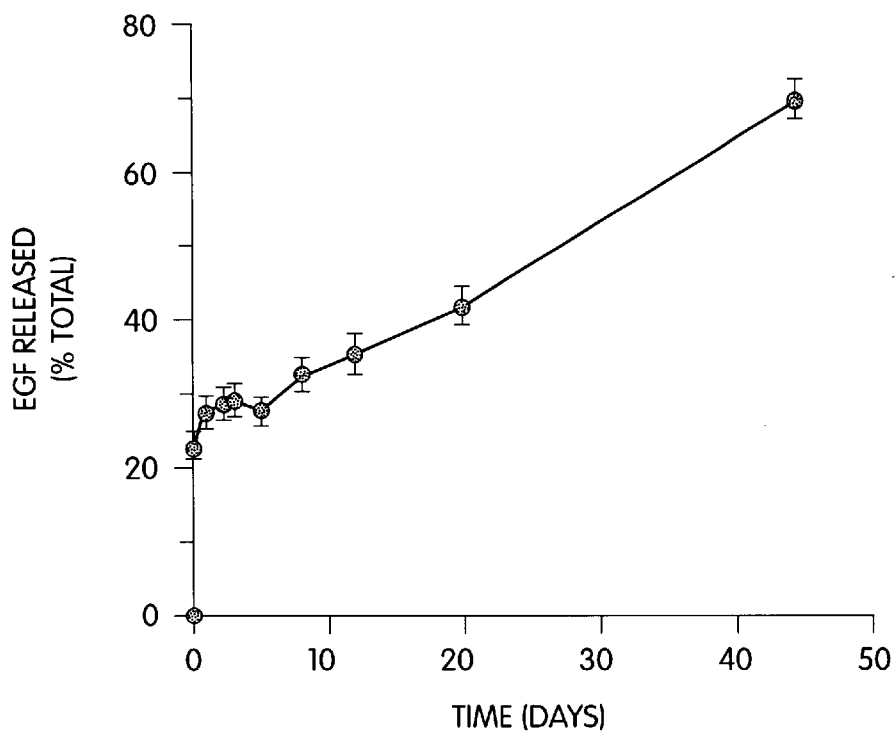
FIG. 2 is a graph of the percent total EGF released continuously over 45 days. Values represent the mean and standard deviation calculated from quadruplicate measurements.

To determine the efficiency of EGF incorporation into microspheres and the release profile from the microspheres, $^{125}$I-labeled EGF was utilized as a tracer. Approximately ½ of the initial EGF (53±11%) was incorporated into microspheres. When EGF-containing microspheres were placed in an aqueous medium, an initial burst of EGF release was noted, as shown in FIG. 2. After this time EGF was released in a steady manner over the remainder of the 30-day time course, as also shown by FIG. 2.

EXAMPLE 2

In Vitro Analysis of the Efficacy of Released EGF

MATERIALS AND METHODS

Cultured hepatocytes were utilized to determine whether the EGF incorporated into and released from microspheres had retained its biological function. Hepatocytes were isolated from Lewis rats using a two-step collagenase perfusion, and purified using a Percoll gradient as previously described by Mooney, et al., (1992), the teachings of which are incorporated herein. Hepatocytes were plated at a density of 10,000 cells/cm$^2$ on 24 well tissue culture dishes coated with 1 µg/cm$^2$ of type I collagen (Collagen Corp., Palo Alto, Calif.) using a carbonate buffer coating technique. Serum-free William's E medium (Gibco, Grand Island, N.Y.) containing insulin (20 mU/ml; Sigma), dexamethasone (5 nM; Sigma), sodium pyruvate (20 mM; Gibco), a mixture of penicillin and streptomycin (100 U/ml; Irvine Scientific, Santa Ana, Calif.), and ascorbic acid (50 µg/ml, fresh daily; Gibco) was used for all experiments. Varying amounts of soluble EGF (Collaborative Research, Bedford, Mass.) were added to the medium in certain experiments. For conditions in which EGF released from microspheres was utilized, medium with no EGF was incubated with EGF containing microspheres for 24–96 hr to allow release of known amounts of EGF, the solution was centrifuged, and the medium containing the released EGF was removed and used in subsequent experiments. To analyze cell entry into S phase of the cell cycle, tritiated thymidine autoradiography was utilized. Cultured hepatocytes were refed 48 hr after plating with medium containing 1 µCi/ml $^3$H-thymidine (NEN; Boston, Mass.) At 72 hr cells were twice washed with PBS to wash out any non-incorporated $^3$H-thymidine, fixed with glutaraldehyde, and dehydrated with 100% methanol. Culture wells were overlaid with NTB-2 emulsion (Kodak; Rochester, N.Y.), and the dishes were allowed to expose for 7 days in complete darkness. Dishes were developed with D-19 developer (Kodak), and photomicrographs of the cells were taken with TMAX-100 film (Kodak) on a Nikon Diaphot microscope using Hoffman optics. In separate experiments to determine the survival and division of cultured hepatocytes over time, the number of hepatocytes present in wells after 1, 4, 6, 8 and 11 of culture was quantitated by removing the cells with a solution of 0.05% Trypsin/0.53 mM EDTA (Gibco) and counted in a Coulter counter.

RESULTS

Figure 3:
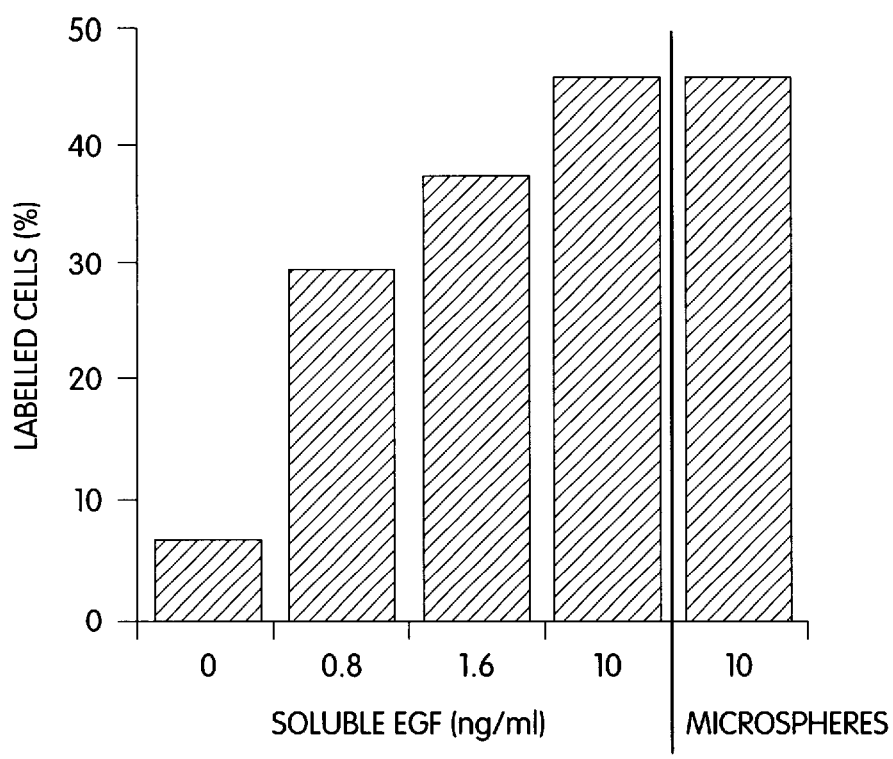
FIG. 3 is a graph quantitating the number of cells with labeled nuclei following $^3$H-thymidine autoradiography, and thus in S phase of the cell cycle. Cells were cultured in medium containing various concentrations of EGF which had not been incorporated into microspheres (Soluble EGF), or in medium containing 10 ng/ml of EGF released from microspheres (Microspheres).
Figure 4:
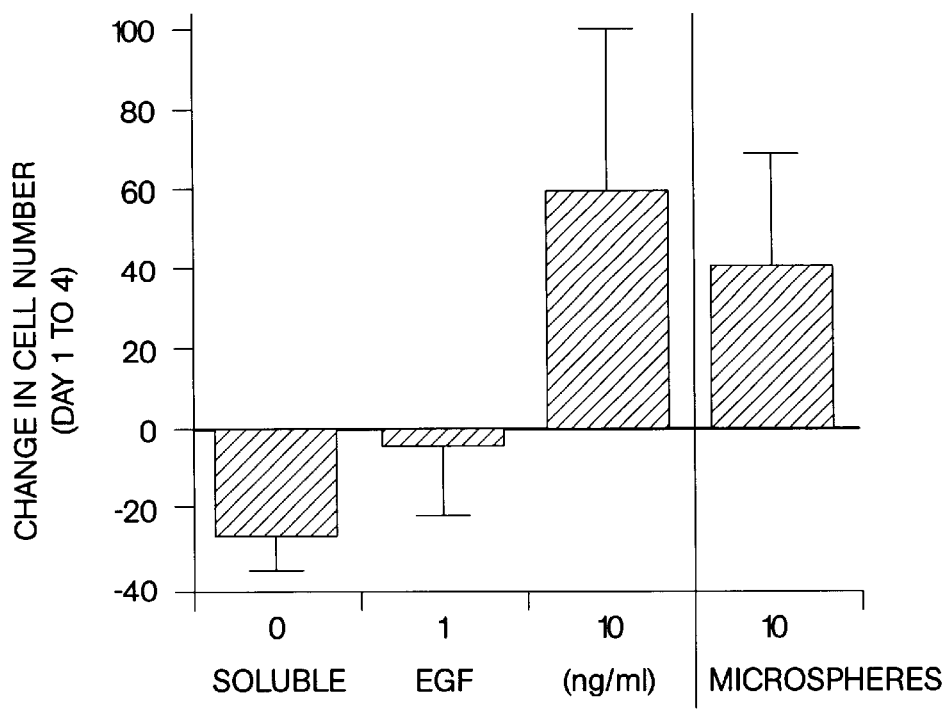
FIG. 4 is a graph of the change in the number of cells present in culture dishes from day 1 to day 4 in medium containing various concentrations of EGF which was not incorporated into microspheres (Soluble EGF) (ng/ml), or in medium containing 10 ng/ml of EGF released from microspheres (Microspheres). Values represent the mean and standard error of the mean calculated from the results of three experiments which were all done in quadruplicate.

The function of EGF released from microspheres was assessed with cultured hepatocytes. EGF containing microspheres were incubated with medium containing no EGF for a set period of time to allow the release of a known amount of EGF (calculated using the release kinetics) into the medium. This medium was utilized in experiments quantitating the number of hepatocytes entering S phase of the cell cycle and subsequently dividing, and the number of surviving hepatocytes over time. EGF which was not incorporated into microspheres stimulated hepatocyte entry into S phase in a dose dependent manner, and the same, saturating dose of this EGF or EGF released from microspheres showed similar stimulation, as demonstrated by FIG. 4. Released EGF also stimulated cell division in a similar manner as control EGF, as the number of cultured hepatocytes increased in a similar manner from day 1 to day 4 when either released EGF or control EGF was utilized, as demonstrated by FIG. 3.

Figure 5:
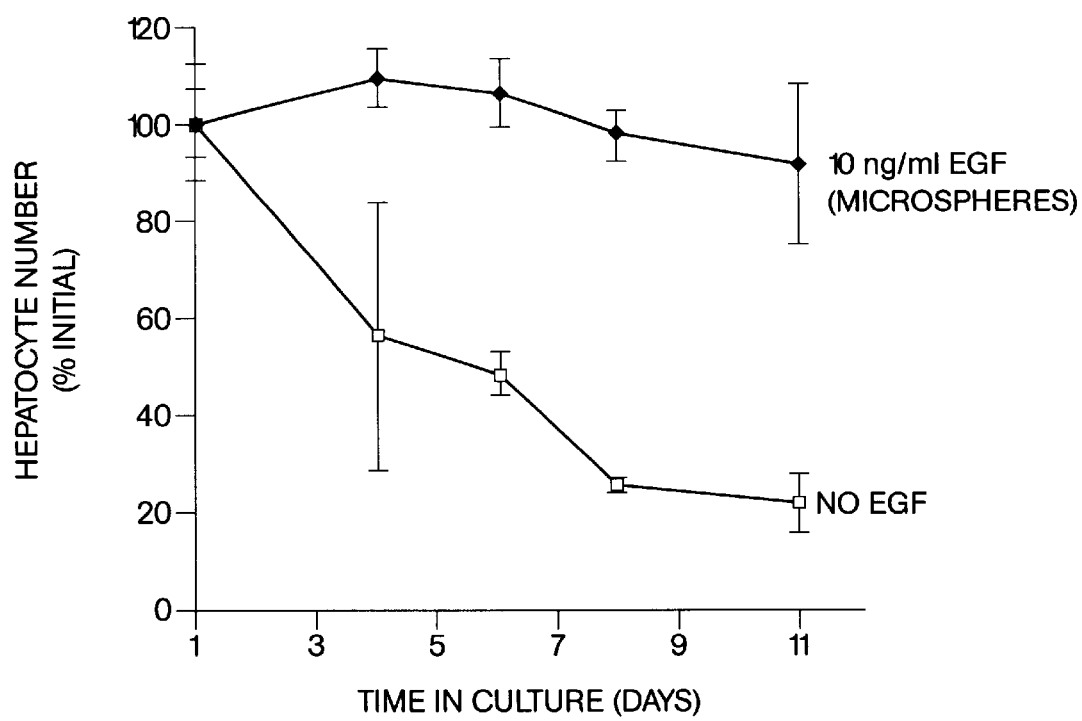
FIG. 5 is a graph of the change in the number of cells present in culture dishes from day 1 to day 11 (expressed as a percentage of the day 1 number) when cultured in medium containing no EGF (No EGF) or in medium containing 10 ng/ml of EGF released from microspheres (microspheres). Values represent the mean and standard deviation calculated from quadruplicate measurements.

Strikingly, not only do hepatocytes not proliferate in medium containing no EGF or a low concentration of soluble EGF (1 ng/ml), but there was actually a decrease in cell number over day 1 to day 4 under these conditions (FIG. 4) which is consistent with cultured hepatocytes requirement for growth factors. Even greater numbers of hepatocytes died over a more extended time in culture under these conditions, but EGF released from the microspheres was largely able to prevent this cell loss, as shown by FIG. 5.

EXAMPLE 3

In Vivo Analysis of EGF Microsphere Co-Transplantation with Hepatocytes

MATERIALS AND METHODS

Isolated and purified hepatocytes were mixed with EGF-containing or control microspheres (0.4 ml×50×10$^6$ hepatocytes/ml+10 mg of microspheres), and seeded onto 95% porous cylindrical sponges (diameter=2.15 cm, thickness=1 mm) fabricated from poly-(L, lactic) acid (Medisorb; Cincinnati, Ohio) and coated with polyvinyl alcohol as previously described technique (17). Cell-polymer devices were implanted into the mesentery of laboratory rats as previously described (18), and ½ of the animals received an end to side portal caval shunt (PCS) one week before cell transplantation (18) to generate systemic stimulating factors. Implants were removed after 14 days, fixed in formalin, and processed for sectioning. Sections of implants were stained with hematoxylin and eosin, and engrafted hepatocytes were identified by their large size, large and spherical nuclei, and distinct cytoplasmic staining. Computerized image analysis (Image Technologies Corp.) was utilized to quantitate the area of each section which was comprised of hepatocytes. The number of hepatocytes per device was calculated by measuring an average hepatocyte area to determine the number of hepatocytes per section, and multiplying by the total volume of the implant divided by the volume of each section. All animals were housed in the Animal Research Facility of Children's Hospital, and NIH guidelines for the care and use of laboratory animals (NIH Publication #85-23 Rev. 1985) have been observed.

RESULTS

EGF-containing microspheres (40 mg) were suspended in 0.4 ml of PBS, seeded onto the porous, biodegradable sponges fabricated from poly-(L-lactic) acid utilized to transplant cells, and implanted for 1 week in the mesentery of Lewis rats to confirm that the microspheres would distribute evenly throughout the devices. Examination of cross-sections of devices removed after one week revealed the relatively even distribution of microspheres throughout the fibrovascular tissue which invades the device over this time.

To determine whether EGF released from microspheres could positively influence the engraftment of hepatocytes transplanted to a heterotopic site, hepatocytes (0.4 ml×5×10$^7$ cells/ml) and microspheres (10 mg) were mixed together and seeded onto porous, biodegradable sponges fabricated from poly-(L-lactic) acid. Cell/microsphere-seeded devices were implanted into the mesentery of laboratory rats, ½ of which had previously received PCS. Retrieval of implants after two weeks, followed by histological preparation and observation, revealed that animals which had a PCS and received EGF containing microspheres appeared to have the greatest number of engrafted hepatocytes. Animals which had a PCS and received control microspheres had fewer engrafted hepatocytes, and animals which did not have a PCS had even less. A thin section of a porous sponge seeded with microspheres and implanted in vivo showed that fibrovascular tissue was present throughout the polymer device at this time, and microspheres (round particles, unstained, 1–30 µm) were visible in virtually all areas of the sponge.

Figure 6:
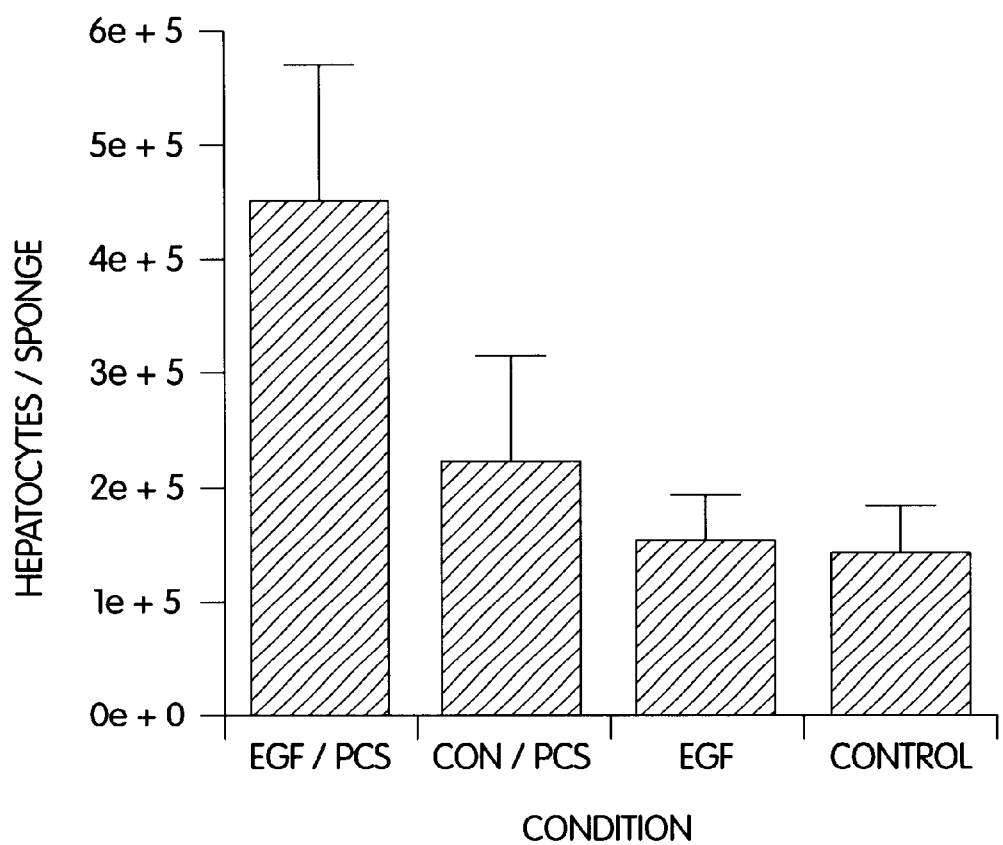
FIG. 6 is a graph quantitating the number of engrafted hepatocytes in sponges removed 14 days after implantation for control microspheres with a PCS (Con/PCS), EGF microspheres without a PCS (EGF), control microspheres without a PCS (Con), and EGF-containing microspheres with a PCS (EGF/PCS). A total of 24 implanted sponges were analyzed (6/ condition), and the values represent the mean and standard deviation. The difference between EGF/PCS and all of the other conditions was statistically significant ($p<0.05$); there no statistically significant difference between any of the other conditions.

Quantitation of these results confirmed that animals with a PCS and EGF microspheres contained two-fold more cells than animals with a PCS and control beads, as shown by FIG. 6. Animals without a PCS, either with EGF or control microspheres, had approximately ⅓ of the number of engrafted hepatocytes as animals with PCS and EGF microspheres, and no statistically significant difference between control and EGF microspheres was found between these groups.

Engrafted hepatocytes were visible in all conditions, along with the host mesenteric tissue, microspheres (round particles, unstained, 1–30 µm), and portions of the polymer sponge.

Modifications and variations of the present invention will be obvious to those skilled in the art from the foregoing detailed description. These modifications and variations are intended to come within the scope of the appended claims.

We claim:

1. A method for delivering a bioactive factor to a transplantation site, said method comprising introducing a microsphere comprising a bioactive factor to a hepatocyte-seeded biodegradable, biocrodible polymer matrix prior to transplantation, wherein said bioactive factor is exposed to portal circulation factors, and wherein said bioactive factor is selected from the group consisting of a growth factor, a factor inhibiting ingrowth of fibrous tissue, and a factor inhibiting cancerous growth, whereby the controlled release of said bioactive factor over time modulates the microenvironment of the transplanted hepatocyte to improve engraftment of the hepatocyte transplanted at the site.

2. The method of claim 1, wherein the factors are selected from the group consisting of heparin binding growth factor, transforming growth factor alpha or beta, alpha fibroblastic growth factor, epidermal growth factor, vascular endothelium growth factor, insulin, glucagon, and estrogen.

3. The method of claim 1, wherein said polymer matrix is a hydrogel polymer solution.

4. The method of claim 3, wherein said cell is seeded in said polymer matrix by suspending it in said hydrogel polymer solution.

5. The method of claim 1, wherein said polymer matrix is a fibrous structure.

6. The method of claim 5, wherein said fibrous structure has interstitial spacing between 100 and 300 microns.

7. The method of claim 1, wherein said transplanted cell is exposed to portal circulation factors by perfoming a portal caval shunt at the time of or prior to implantation of said cells.

8. The method of claim 1, wherein said microsphere comprises a polymer.

9. The method of claim 8, wherein said polymer is comprised of poly(lactide), poly(glycolic acid), poly(lactide-co-glycolide), poly(caprolactone), polycarbonate, polyamide, polyanhydride, polyamino acid, polyolthoester, polyacetal, polycyanoacrylate, polyurethane, polyacrylate, ethylene-vinyl acetate, acyl substituted cellulose acetate, polystyrene, polyvinyl chloride, polyvinyl fluoride, poly(vinyl imidazole), chlorosulphonated polyolefin, or polyethylene oxide.

* * * * *

UNITED STATES PATENT AND TRADEMARK OFFICE
CERTIFICATE OF CORRECTION

PATENT NO.    : 6,281,015 B1
DATED         : August 28, 2001
INVENTOR(S)   : David J. Mooney et al.

It is certified that error appears in the above-identified patent and that said Letters Patent is hereby corrected as shown below:

Title page,
Item [56], in OTHER PUBLICATIONS, replace "Allcock et al., "An Ionically Cross-Linkable Polyphosphazene: Poly[bis(carboxylatophenoxy) phosphazene] an Its Hydrogels and Membranes," *Macromolecules* 22:75-79 (1989)" with -- Allcock et al., "An Ionically Cross-Linkable Polyphosphazene: Poly[bis(carboxylatophenoxy) phosphazene] and Its Hydrogels and Membranes," *Macromolecules* 22:75-79 (1989) --;
Within the Asonuma et al. reference, replace "Quantitization" with -- Quantitation --;
Within the Wilson et al. reference, replace "hypercholestremia" with -- hypercholesteremia --;
Within the Vital Statics of the United States reference, replace "vol." with -- Vol. --;
Within the Annual Report of the Scientific Registry for Organ Transplantation and The Organ Procurement and Transplantaion Network reference, replace "Scientific" with -- U.S. Scientific --;
Within the title of the *Chemistry and Industry* reference, replace "Absorable" with -- Absorabable -- and replace "95" with -- 905 --;

Column 10,
The line below line 25, the figure should be labeled -- where n is an integer --;

Column 12,
Line 61, replace "Wilson;" with -- Wilson, --; and

Column 18,
Line 10, replace "biocrodible" with -- bioerodible --.

Signed and Sealed this

Twenty-eighth Day of May, 2002

*Attest:*

*Attesting Officer*

JAMES E. ROGAN
*Director of the United States Patent and Trademark Office*